United States Patent [19]

Reithofer

[11] Patent Number: 5,527,269
[45] Date of Patent: Jun. 18, 1996

[54] ANKLE JOINT ORTHESIS

[75] Inventor: Alfred Reithofer, Rosenheim, Germany

[73] Assignees: Medi Bayreuth GmbH & Co., Bayreuth; Paromed Medizintechnik GmbH, Neubeuern, both of Germany

[21] Appl. No.: 358,717

[22] Filed: Dec. 19, 1994

[30] Foreign Application Priority Data

Dec. 24, 1993 [DE] Germany .............................. 9319990 U

[51] Int. Cl.⁶ ........................................................ A61F 5/00
[52] U.S. Cl. ............................................. 602/27; 607/111
[58] Field of Search ...................................... 602/5, 27–29, 602/62, 65, 66; 607/108, 111

[56] References Cited

U.S. PATENT DOCUMENTS

| | | |
|---|---|---|
| Re. 34,661 | 7/1994 | Grim . |
| 487,492 | 12/1892 | Pugsley . |
| 1,465,233 | 8/1923 | Posner . |
| 2,694,395 | 11/1954 | Brown . |
| 2,774,152 | 12/1956 | Alber . |
| 2,800,900 | 7/1957 | Schultz ...................................... 602/27 |
| 2,830,585 | 4/1958 | Weiss . |
| 3,548,420 | 12/1970 | Spence . |
| 3,628,537 | 12/1971 | Berndt et al. . |
| 3,663,973 | 5/1972 | Spence . |
| 3,674,023 | 7/1972 | Mann ...................................... 602/65 |
| 3,717,145 | 2/1973 | Berndt et al. . |
| 3,780,537 | 12/1973 | Spencer . |
| 3,858,379 | 1/1975 | Graves et al. . |
| 3,885,403 | 5/1975 | Spencer . |
| 3,889,684 | 6/1975 | Lebold . |
| 3,900,035 | 8/1975 | Welch et al. . |
| 4,055,188 | 10/1977 | Pelton . |
| 4,092,982 | 6/1978 | Salem . |
| 4,243,041 | 1/1981 | Paul . |
| 4,280,489 | 7/1981 | Johnson, Jr. . |
| 4,821,743 | 4/1989 | Wetz ...................................... 602/27 X |
| 4,964,402 | 10/1990 | Grim et al. . |
| 4,966,134 | 10/1990 | Brewer . |
| 5,007,416 | 4/1991 | Burns et al. . |
| 5,088,478 | 2/1992 | Grim . |
| 5,113,877 | 5/1992 | Johnson et al. . |
| 5,125,400 | 6/1992 | Johnson, Jr. . |
| 5,199,941 | 4/1993 | Makinen . |
| 5,226,875 | 7/1993 | Johnson ...................................... 602/27 |
| 5,366,439 | 11/1994 | Peters . |
| 5,370,133 | 12/1994 | Darby et al. . |
| 5,376,068 | 12/1994 | Grifka . |

FOREIGN PATENT DOCUMENTS

| | | |
|---|---|---|
| 0297157 | 1/1989 | European Pat. Off. . |
| 1928411 | 9/1965 | Germany . |
| 8700201 | 2/1987 | Germany . |
| 3537360 | 2/1987 | Germany . |
| 3742352 | 6/1989 | Germany . |
| 3803304 | 8/1989 | Germany . |
| 8907464 | 9/1989 | Germany . |
| 3924428 | 2/1990 | Germany . |
| 9004108 | 6/1990 | Germany . |
| 8902601 | 7/1990 | Germany . |
| 9015508 | 3/1992 | Germany . |
| 9208689 | 9/1992 | Germany . |
| 9319990 | 3/1994 | Germany . |
| 33751 | 5/1959 | Switzerland . |
| 678808A5 | 11/1991 | Switzerland . |
| 740621 | 11/1965 | United Kingdom . |
| 8809156 | 12/1988 | WIPO . |

*Primary Examiner*—Linda C. Dvorak
*Attorney, Agent, or Firm*—Thomas R. Vigil; Larry J. Chapa

[57] ABSTRACT

The ankle joint orthesis for the stabilization of the internal and external ankle joint comprises a medial shell and a lateral shell made of plastic. The shells extend from the heel region beyond the malleolus to the lower calf region. The shells are lined throughout the entire support surface with a flexible padding. Loop and hook type fastening structure are provided for fastening and securing the shells. One shell, preferably the lateral shell, is of an L-shaped design and has a laterally extending leg which extends below the foot between the heel and the ball of the foot. Both shells can be connected to each other by loop and hook type fastening structure under the foot, e.g., a selectively adhesive strap fastened to one of the shells and passing under the foot for being adhesively secured to a mating strap closure on the other shell. Both shells have openings in the malleolar area.

6 Claims, 2 Drawing Sheets

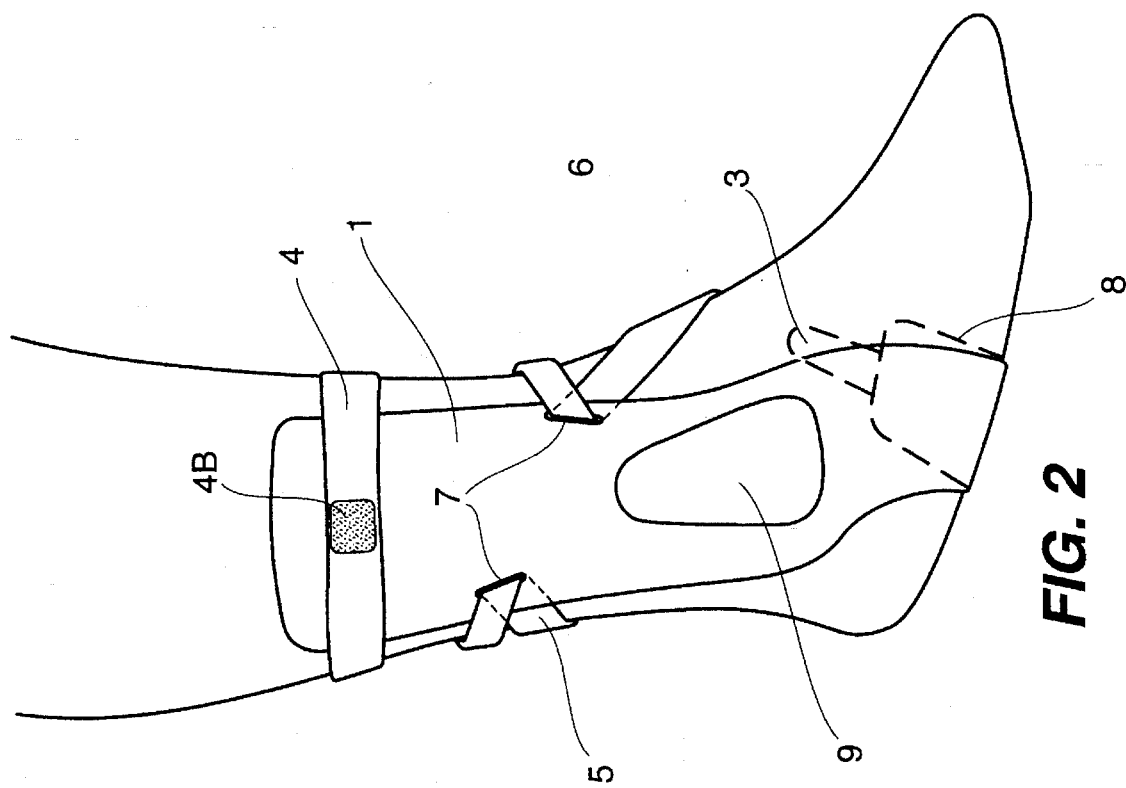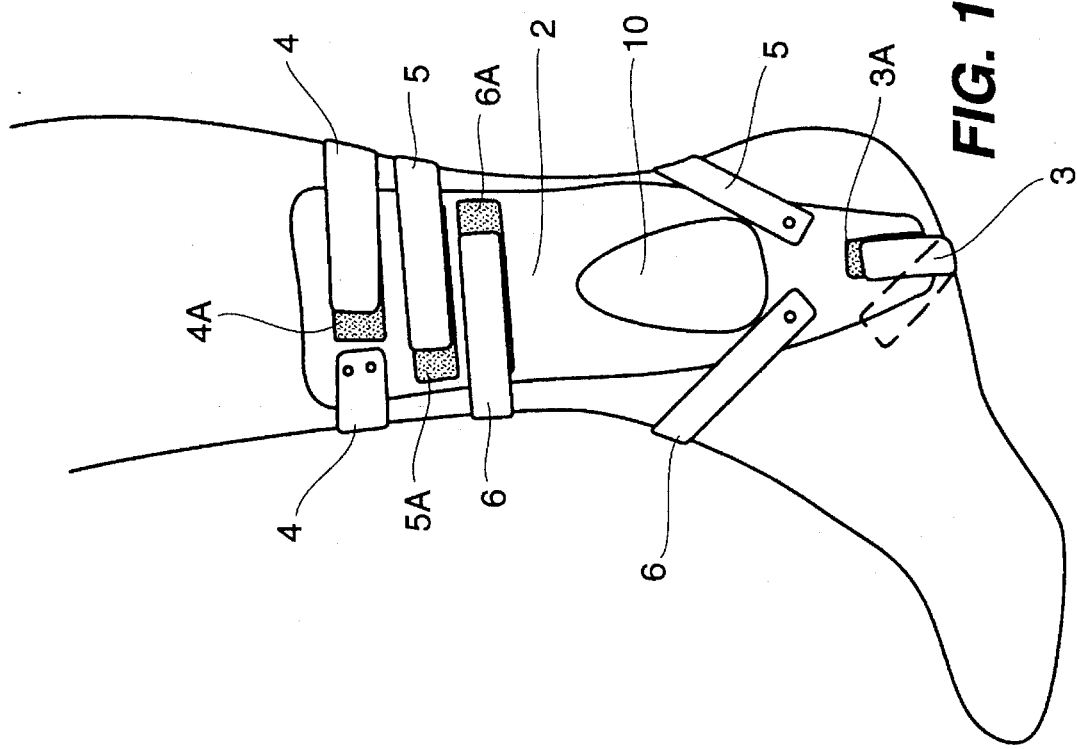

ANKLE JOINT ORTHESIS

BACKGROUND OF THE INVENTION

1. Field of the Invention

The present invention relates to an ankle joint orthesis for the stabilization of the internal and external ankle joint. Preferably, the ankle joint orthesis comprises a medial shell and a lateral shell made of plastic which extend from the heel region beyond the malleolus to the lower calf region. The shells are lined throughout their entire support surface with a flexible padding and fastening structure, such as Velcro® closures, are provided for fastening and securing the shells together. One shell, preferably the lateral shell, is of an L-shaped design and has a laterally extending leg which extends and catches below the foot between the heel and the ball of the foot. Both shells also can be connected to each other by fastening structure, such as by Velcro® tape, which extends under the foot and both shells have openings in the malleolar area.

2. Description of the Related Art Including Information Disclosed Under 37 CFR §§1.97–1.99

Over the years, various ankle support devices and ankle joint orthesis devices have been proposed and examples of devices which are analogous and non-analogous to the ankle joint orthesis of the present invention are disclosed in the following U.S. and foreign patent publications:

| U.S. Pat. No. | Patentee |
|---|---|
| 487,492 | Pugsley |
| 1,465,233 | Posner |
| 2,694,395 | Brown |
| 2,774,153 | Alber |
| 2,830,585 | Weiss |
| 4,280,489 | Johnson, Jr. |
| 4,869,267 | Grim, et al. |
| 4,964,402 | Grim, et al. |
| 4,966,134 | Brewer |
| 5,007,416 | Burns et al. |
| 5,088,478 | Grim |
| 5,125,400 | Johnson, Jr. |
| 5,199,941 | Makinen |
| RE 34,661 | Grim |
| German Published Patent Applications: | |
| DE 29 13 606 | Johnson |
| DE 35 37 360 | Kühnreich |
| DE 37 42 352 | Mulligan |
| DE 39 24 428 | Rau |
| German Published Utility Models and Gebrauchsmusters: | |
| DE-U-19 28 411 | Dassler |
| G 89 02 601 | Jung |
| G 89 07 464 | Saniewy Medizinische Lagerungstechnik GmbH |
| G 90 04 108 | Rexing Orthopädie-Technik |
| G 90 15 508 | Kleylein |
| G 92 08 689 | Heinrich Ad. Berkemann Gmbh |
| British Patents: | |
| GB 740, 621 | Société Pneuma-Jact |
| Swiss Patents: | |
| CH 337,751 | Schuhfabrik Henke & Co. Aktiengesellschaft |
| CH 678,808 | Amrein |

The Johnson U.S. Pat. No. 4,280,489 (Equivalent to German Patent No. DE-C-29 13 606) discloses an ankle joint orthesis for the stabilization of the internal and external ankle joint. The ankle joint orthesis comprises a medial shell and a lateral shell made of plastic. The shells extend from the heel region beyond the malleolus to the lower calf region. The shells are lined throughout the entire support surface with a flexible padding, namely air inflatable bladders and Velcro® closures are provided for fastening and securing the shells together.

U.S. Pat. No. 4,964,402 (Equivalent to PCT Published Patent Application No. WO 90/01911) discloses an orthopedic arrangement with gel cushions, which is placed in shell-like fashion around limbs, and which can be cooled or heated.

The German Patent Publication DE-U-89 07 464 discloses a stirrup-like ankle joint orthesis in one part with openings for the heel and the malleoli.

As will be described in greater detail hereinafter, the ankle joint orthesis of the present invention differs from the previously proposed ankle joint orthesis by providing an ankle joint orthesis which facilitates a high level of stabilization for the ankle joint, which effectively reduces pushing forward of the talus, which can be worn without discomfort, and which can be easily fastened around the ankle.

SUMMARY OF THE INVENTION

According to the present invention there is provided an ankle joint orthesis for the stabilization of the internal and external ankle joint comprising a medial shell and a lateral shell made of plastic. The shells extend from the heel region beyond the malleolus to the lower calf region. The shells are lined throughout the entire support surface with a flexible padding. Fastening structure, such as Velcro® closures, are provided for fastening and securing the shells. One shell, preferably the lateral shell, is of an L-shaped design and has a laterally extending leg which catches below the foot between the heel and the ball of the foot. Both shells can be connected to each other by means of a Velcro® tape under the foot, e.g., a Velcro® tape fastened to one of the shells and passing under the foot for being secured to a Velcro® closure on the other shell. Both shells have openings in the malleolar area. An optimal distribution of pressure throughout the entire support surface is achieved by the pads on the inside of the shells. The L-shape of one of the shells facilitates an improved foothold.

Advantageously, the padding, which may be a silicon padding, preferably a sheath filled with liquid or gel-like silicon, extends beyond the openings.

In the upper portion, the shells can be secured by means of a Velcro® tape running around the calf in annular fashion. Optimal fastening around the ankle joint is achieved by the circumstance that in the middle sector the shells can be fastened around the ankle joint and the lower calf with Velcro® tapes, which are securable above the malleolus medialis and run in front and the back from a midline below the malleolus medialis to laterally beyond the malleolus lateralis, where they are reversed.

Reversal is achieved simply by means of slots in the lateral shell.

The ankle joint orthesis of the present invention is suited for the post-operative, conventional as well as preventive treatment of ankle joint injuries.

BRIEF DESCRIPTION OF THE DRAWINGS

The invention is described hereinafter with reference to the drawings FIGS. described below:

FIG. 1 is a medial view of an ankle joint orthesis.

FIG. 2 is a lateral view of an ankle joint orthesis.

DESCRIPTION OF THE PREFERRED EMBODIMENT(S)

Figure 4:
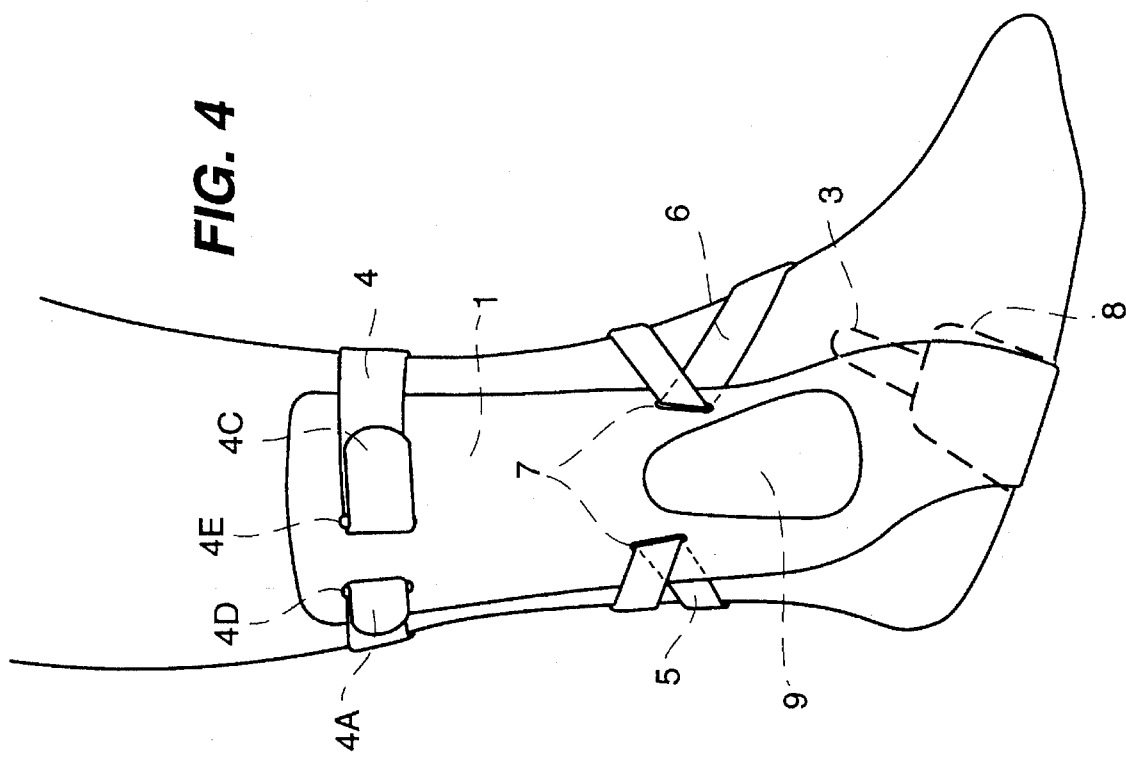
FIG. 4 is a lateral view of a modification of the ankle joint orthesis shown in FIGS. 1 and 2.

As shown in FIGS. 1 and 2, the ankle joint orthesis shown therein comprises a medial shell 2 and a lateral shell 1 made of plastic. Shells 1 and 2 extend from the heel region beyond the malleolus into the lower calf region. Lateral shell 1 is of L-shaped design and includes a laterally extending leg that catches under the foot between the heel and ball of the foot. Both shells 1 and 2 can be connected by means of a Velcro® tape 3 under the foot. In this respect, a Velcro® tape 3 can be fastened to a tongue 8 of the lateral shell 1 and arranged to pass under the foot and can be secured to a Velcro® closure 3a on the medial shell 2. Both shells 1 and 2 are provided with openings 9, 10 in the malleolar area.

In their upper sector, shells 1 and 2 can be secured by means of a Velcro® tape 4, which runs around the calf in annular fashion, to Velcro® closures 4a, 4b and 4c on both shells 1 and 2. The ends of Velcro® tape 4 are reversed about reversal webs 4d, 4e which can also be provided with reversal rollers, and secured onto themselves. In the middle sector, the shells 1 and 2 are fastened around the ankle joint and the lower calf with Velcro® tapes 5, 6 which are securable to medial shell 2 above the malleolus medialis and run in the front and the back from a midline below the malleolus medialis to laterally beyond the malleolus lateralis where they are reversed. They are reversed by means of slots 7 in the lateral shell 1.

Figure 3:
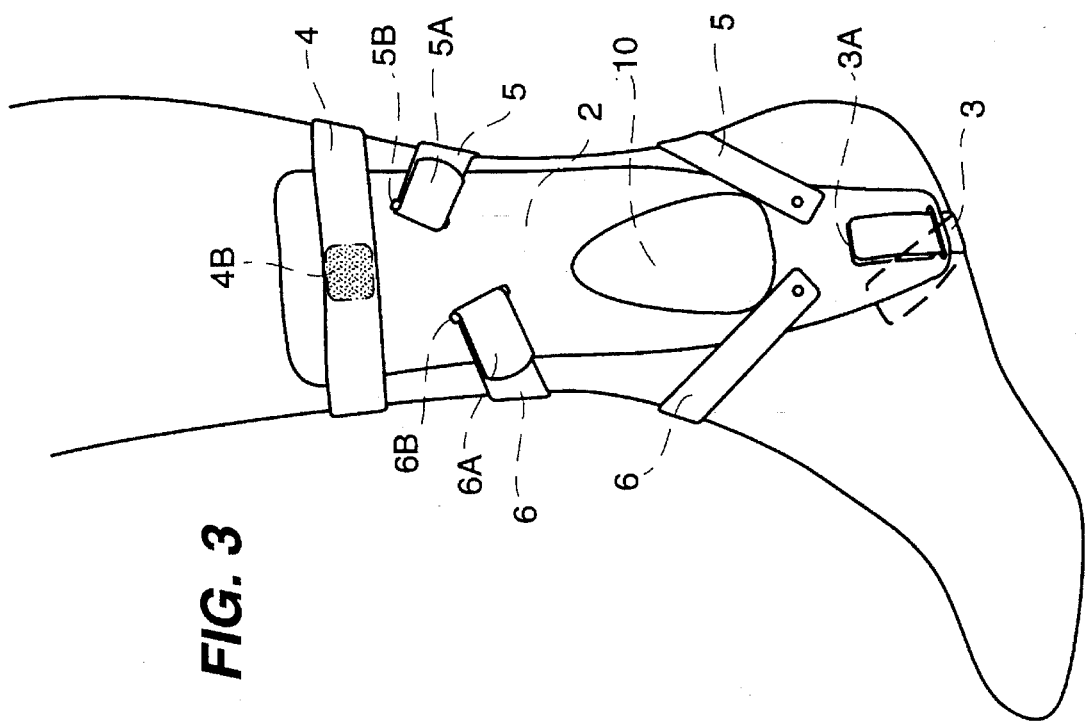
FIG. 3 is a medial view of a modification of the ankle joint orthesis shown in FIGS. 1 and 2.

The modification shown in FIGS. 3 and 4 is related to the closures of Velcro® tapes 4, 5 and 6. Here, too, the ankle joint orthesis comprises a medial shell 2 and a lateral shell 1 made of plastic. Shells 1 and 2 extend from the heel region beyond the malleolus to the lower calf region. Lateral shell 1 is L-shaped in design and has a laterally extending leg which extends beneath and catches with a tongue 8 under the foot between the heel and the ball of the foot. Both shells 1 and 2 can be connected under the foot by means of a Velcro® tape 3. The Velcro® tape 3 is fastened to a tongue 8 of the lateral shell 1 and passes under the foot and can be secured on the medial shell 2 to a Velcro® tape 3a. Both shells 1 and 2 are provided with openings 9 and 10 in the malleolar area.

In their upper sector, the shells 1 and 2 can be secured to Velcro® closures 4a, 4b and 4c on both shells 1 and 2 at the calf by means of Velcro® tape 4 which runs around the calf in annular fashion. The ends of the Velcro® tape 4 are reversed about reversal webs 4d and 4e, which can also be provided with reversal rollers, and secured onto themselves. In the middle sector, the shells 1 and 2 are fastened around the ankle joint and the lower calf to Velcro® closures 5a, 6a with Velcro® tapes 5, 6, which are securable to the medial shell 2 above the malleolus medialis and which pass in the front and the back from a midline below the malleolus lateralis, where they are reversed. They are reversed by means of slots 7 in lateral shell 1, and the Velcro® closures 5a and 6a are fastened by reversing the ends via reversal webs 5b, 6b, which also may be provided with reversal rollers.

I claim:

1. An ankle joint orthesis for the stabilization of the internal and external ankle joint, said ankle joint orthesis comprising:

a medial shell and a lateral shell made of plastic;

said shells adapted to extend from the heel of a foot to the lower calf region;

said shells being lined throughout the entire support surface with a flexible padding;

fastening structure being provided for fastening and securing said shells together while creating a space for receiving a foot;

said lateral shell being of an L-shaped design and having a laterally extending leg which is adapted to extend below said space for the foot and shaped to conform to the space between the heel and the ball of the foot;

both shells being connected to each other by means of said fastening structure fastened to one of the shells and passing under said space for said foot and being secured to the other shell; and, both shells having openings for receiving protruding portions in the malleolar area of the foot.

2. An ankle joint orthesis according to claim 1 characterized in that the padding extends beyond the openings of both shells.

3. An ankle joint orthesis according to claim 1 characterized in that the padding is a silicon padding.

4. An ankle joint orthesis according to claim 3 characterized in that the padding is a sheath filled with a liquid gel silicon.

5. An ankle joint orthesis according to claim 1 characterized in that the upper portion of the shells can be secured at the lower calf region of said shells by means of loop and hook fastening structure including at least one calf strap extending around said shells in annular fashion.

6. An ankle joint orthesis according to claim 5 characterized in that in the front and back of the orthesis, the middle portion of said shells are fastened around the ankle joint and the lower calf with said fastening structure including loop and hook fastening means and at least two ankle straps securable to said medial shell and each strap extending from below said opening in said medial shell, to one of two slots in said lateral shell, each strap making a reversal and extending back around said ankle joint orthesis back to said medial shell above said opening in said medial shell, with at least one of said ankle straps extending around the front of said ankle joint orthesis, and at least one of said ankle straps extending around the back of said ankle joint orthesis to said lateral shell.

* * * * *